(12) United States Patent
York et al.

(10) Patent No.: US 7,943,576 B2
(45) Date of Patent: May 17, 2011

(54) METHODS OF USING ENTEROSTATIN AS INHIBITOR OF ANGIOGENESIS

(75) Inventors: David A. York, Logan, UT (US); Mie Jung Park, Logan, UT (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 184 days.

(21) Appl. No.: 12/095,523

(22) PCT Filed: Nov. 27, 2006

(86) PCT No.: PCT/US2006/045528
§ 371 (c)(1),
(2), (4) Date: Oct. 10, 2008

(87) PCT Pub. No.: WO2007/064634
PCT Pub. Date: Jun. 7, 2007

(65) Prior Publication Data
US 2010/0215614 A1    Aug. 26, 2010

Related U.S. Application Data

(60) Provisional application No. 60/741,500, filed on Nov. 30, 2005.

(51) Int. Cl.
A61K 38/00 (2006.01)
A61K 38/08 (2006.01)
A61K 38/17 (2006.01)
A61P 35/00 (2006.01)
C07K 14/515 (2006.01)

(52) U.S. Cl. ..... 514/13.3; 514/1.1; 514/21.8; 514/21.92
(58) Field of Classification Search .......... None
See application file for complete search history.

(56) References Cited

U.S. PATENT DOCUMENTS
2005/0054634 A1* 3/2005 Busch et al. ............... 514/215

OTHER PUBLICATIONS

Barton C. et al., "Differential effects of enterostatin, galanin and opioids on high-fat diet consumption," Brain Res., vol. 702, pp. 55-60 (1995).
Berger K. et al., "Binding of enterostatin to the human neuroepithelioma cell line SK-N-MC," Peptides, vol. 19: pp. 1525-1531 (1998).
Berger, K. et al., "Mitochondrial ATP synthase—a possible target protein in the regulation of energy balance in vitro and in vivo," Nutrit. Neurosci, vol. 5, pp. 201-210 (2002).
Bicknell, R. "Vascular targeting and the inhibition of angiogenesis," Annals of Oncology, vol. 5, pp. 45-50 (1994).
Bowyer, R. C. et al., "The effect of a satiating meal on the concentrations of procolipase activation peptide in the serum and urine of normal and morbidly obese individuals," Gut., vol. 34, pp. 1520-1525 (1993).
Chang S. et al., "Interaction of the C-terminal domain of p43 and the—subunit of ATP synthase: its functional implication in endothelial cell proliferation," J. Biol. Chem, vol. 277; pp. 8388-8394 (2001).
Creamer, D. et al., "Overexpression of the angiogenic factor platelet-derived endothelial cell growth factor/thymidine phosphorylase in psoriatic epidermis," Br. J. Dermatol., vol. 137, pp. 851-855 (1997).
Das B. et al., "A novel ligand in lymphocyte mediated cytotoxicity: expression of beta subunit of H+ transporting ATP synthase on the surface of tumor cell lines," J. Exp. Med., vol. 180, pp. 273-281 (1994).
Eerola, A.K. et al., "Tumour infiltrating lymphocytes in relation to tumour angiogenesis, apoptosis," Lung Cancer, vol. 26, pp. 73-83 (1999).
Erlanson-Albertsson, C. et al., "Enterostatin—A peptide regulating fat intake," Obesity Res, vol. 5, pp. 360-372 (1997).
Erlanson-Albertsson, C. et al., "A possible physiological function of procolipase activation peptide in appetite regulation," Biochimie, vol. 70, pp. 1245-1250 (1988).
Erlanson-Albertsson, C. et al., "Pancreatic procolipase propeptide, enterostatin, specifically inhibits fat intake," Physiol. Behav., vol. 49, pp. 1191-1194 (1991).
Gasparini, B., "The rationale and future potential of angiogenesis inhibitors in neoplasia," Drugs, vol. 58, pp. 17-38 (1999).
Halford J, et al., "Serotonin (5HT) and serotionin receptors in the regulation of macronutrient intake In: Neural and Metabolic Control of Macronutrient," intake eds HR Berthoud et al., pp. 425-446 CRC Press, Boca Raton. (2000).
Imamura, M. et al., "Distribution and characterization of enterostatin-like immunoreactivity in human cerebrospinal fluid," Peptides, vol. 19, pp. 1385-1391 (1998).
Lin L. et al., "Amygdala enterostatin induces c-Fos expression in regions of hypothalamus that innvervate the PVN," Brain Res., Sep 10; vol. 1020(1-2), pp. 147-153 (2004).
Lin, L. et al., "b-casomorphins stimulate and enterostatin inhibits the intake of dietary fat in rats," Peptides, vol. 19, pp. 325-331 (1998).
Lin, L. et al.1, Changes in the microstructure of feeding after administration of enterostatin into the paraventricular nucleus and the amygdala, Peptides, vol. 19, pp. 557-562 (1998).

(Continued)

*Primary Examiner* — Robert Landsman
(74) *Attorney, Agent, or Firm* — Bonnie J. Davis; John H. Runnels (57) ABSTRACT

It has been discovered that enterostatin inhibits angiogenesis in an in vitro adipose tissue angiogenesis model. In concentrations from about $10^{-6}$ to about $10^{-9}$ M, enterostatin effectively blocked the angiogenic response. Enterostatin will be effective in treating noncancerous and cancerous diseases that involve an increase in angiogenesis, e.g., rheumatoid arthritis, retinopathy of prematurity, neovascular glaucoma, diabetic retinopathy, and psoriasis. This, antiangiogenic activity was confirmed in two additional tissue cells lines (liver and neuronal cells) using a microarray analysis.

8 Claims, 5 Drawing Sheets

OTHER PUBLICATIONS

Lin, L. et al., "Chronic icv enterostatin preferentially reduced fat intake and lowered body weight," Peptides, vol. 18, pp. 657-661 (1997).

Lin, L. et al., "Comparisons of the effects of enterostatin on food intake and gastric emptying in rats," Brain Res, vol. 745, pp. 205-209, (1997).

Lin, L., Gehlert, D.R. et al., "Effect of enterostatin on the feeding responses to galanin and NPY, Obes. Res." vol. 1, pp. 186-192 (1993).

Lin, L.. et al., "Enterostatin actions in the amygdala and PVN to suppress feeding in the rat," Peptides, vol. 18, pp. 1341-1347 (1997).

Lin, L. et al., "Enterostatin suppresses food intake in rats after near celiac and intracarotid arterial injection," Am. J. Physiol. Reg Integr Comp Physiol. May; vol. 278No. 5):R1346-51 (2000).

Lin L. et al., "Procolipase gene and enterostatin expression in the rat brain," FASEB vol. J; p. A783, (2002).

Lin, L. et al., "Structural requirements for the biological activity of enterostatin," Peptides, vol. 15, pp. 849-854 (1994).

Lin L. et al., "The enterostatin inhibition of dietary fat intake is dependent upon CCKA receptors," Am. J. Physiology, vol. 285, No. 2 pp. R321-R328 (2003).

Maniotis, A.J. et al., "Vascular channel formation by human melanoma cells in vivo and in vitro: Vasculogenic mimicry," Am. J. Pathol., vol. 155, pp. 739-752 (1999).

Martinez, L.O. et al., "Ectopic beta-chain of ATP synthase is an apolipoprotein A-I receptor in hepatic HDL endocytosis," Nature (Lond) vol. 421, pp. 75-79 (2003).

Mei, J. et al., "Effect of enterostatin given intravenously and intracerebroventricularly on high-fat feeding in rats," Regul. Pept., vol. 41, pp. 209-218 (1992).

Mei, J. et al., "Enterostatin—its ability to inhibit insulin secretion and to decrease high-fat food intake," Int. J. Obesity, vol. 17, pp. 701-704 (1993).

Mei, J. et al., "Identification of enterostatin, the pancreatic procolipase activation peptide, in the intestine of rat: effect of CCK-8 and high-fat feeding," Pancreas, vol. 8, pp. 488-493 (1993).

Mei, J. et al., "Inhibition of insulin by intraduodenally infused VPDPR in rats," Peptides, vol. 18, pp. 651-657 (1997).

Mei, J. et al., "Plasma insulin response to enterostatin and effect of adrenalectomy in rat," Obes. Res., vol. 4, pp. 513-519 (1996).

Mei, J. et al., "Role of intraduodenally administered enterostatin in rat: inhibition of food intake," Obes. Res., vol. 4, pp. 161-165 (1996).

Miner, J.L. et al., "Reduction of feed intake in sheep by enterostatin, the procolipase activation peptide," J. Anim. Sci., vol. 72, pp. 1578-1582 (1994).

Moser, T. et al., Angiostatin binds ATP synthase on the surface of human endothelial cells, Proc. Natl. Acad. Sci., vol. 96, pp. 2811-2816 (1999).

Nagase, H. et al., "Effect of galanin and enterostatin on sympathetic nerve activity to interscapular brown adipose tissue," Brain Res., vol. 709, pp. 44-50 (1996).

Nagase, H.A. et al., "Regulation of feeding behavior, gastric emptying, and sympathetic nerve activity to interscapular brown adipose tissue by galanin and enterostatin: the involvement of vagal-central nervous system interactions," J. Gastroenterol., vol. 37, Suppl 14, pp. 118-127 (2002).

Okada, S. et al., "Chronic effects of intracerebral ventricular enterostatin in Osborne-Mendel rats fed a high-fat diet," Physiol. Behav., vol. 54, pp. 325-330 (1993).

Okada, S. et al., "Differential inhibition of fat intake in two strains of rat by the peptide enterostatin," Amer. J. Physiol., vol. 262, pp. R1111-R1116 (1992).

Okada, S. et al., "Enterostatin (Val-Pro-Asp-Pro-Arg) the activation peptide of procolipase selectively reduces fat intake,"Physiol. Behav., vol. 49, pp. 1185-1189 (1991).

Okada, S. et al., "Procolipase mRNA: Tissue localization and effects of diet and adrenalectomy," Biochem. J., vol. 292, pp. 787-789 (1993).

Ookuma, K. C. et al., "Effect of enterostatin and kappa-opioids on macronutrient selection and consumption," Peptides, vol. 18, pp. 785-791 (1997).

Ookuma, M. et al., "York. Inhibition of insulin release by enterostatin," Int. J. Obesity vol. 22, pp. 800-805 (1998).

Park et al., "The F(1)-ATPase beta-subunit is the putative enterostatin receptor," SLIDE (2004).

Park, M. et al., "The F1-ATPase Beta subunit is the putative Enterostatin Receptor," Peptides, vol. 25, pp. 2127-2133 (2004).

Pierzynowski, S. G. et al., "Possible integration of the electrical activity of the duodenum and pancreas secretion through enterostatin," Biomed. Res., vol. 15, pp. 257-260 (1994).

Rippe, C. et al., Effect of high fat diet, surrounding temperature and enterostatin on uncoupling protein gene expression. Am. J. Physiol., vol. 279; pp. E293-E300 (2000).

Rodriguez-Gallardo, J. et al., "Inhibitory effect of enterostatin on the beta cell response to digestive insulinotropic peptides," Int J Obes Relat Metab Disord, vol. 23, No. 8, pp. 787-792 (1999).

Rosen, L., "Antiangiogenic strategies and agents in clinical trials," Oncologist, vol. 5, supplement 1, pp. 20-27 (2000).

Rössner, S. et al., "Intravenous enterostatin does not affect single meal food intake in man," Appetite, vol. 34, pp. 37-42 (1995).

Rupnick, M.A. et al., "Adipose tissue mass can be regulated through the vasculature," PNAS, vol. 99, pp. 10730-10735 (2002).

Smeets, M.P. et al., "The effect of oral enterostatin on hunger and food intake in human volunteers," FASEB J , vol. 13, No. 5, p. A871 (1999 (Abs).

Smith, B.K. et al., "Chronic d-fenfluramine treatment reduces fat intake independent of macronutrient preference," Pharmacology Biochem. & Behavior, vol. 60, pp. 105-114 (1998).

Sörhede, M. et al., "Enterostatin is produced in three different forms in the rat intestine," Int. J. Obesity, vol. 19, p. 115 (1995).

Tadayyon, M. et al., "Structure-function studies on enterostatin inhibition of insulin release," Intl J Diabetes & Metabolism, vol. 10, pp. 14-21 (2002).

Takenaka, Y. et al., :"Enterostatin (VPDPR) and its peptide fragment DPR reduce serum cholesterol levels after oral administration in mice," Biosci. Biotechnol. Biochem, vol. 67, pp. 1620-1622 (2003).

Tian, Q. et al., "Vagal-central nervous system interactions modulate the feeding response to peripheral enterostatin," Obes. Res., vol. 2, pp. 527-534 (1994).

Townsley, M.I. et al., "Enterostatin efflux in cat intestinal lymph: Relation to lymph flow, hyaluronan and fat absorption," Am. J. Physiol., vol. 271, pp. G714-G721 (1996).

Weatherford, S. C. et al., "Intraventricular administration of enterostatin decreases food intake in baboons," Appetite, vol. 19, p. 225 (1992).

Wenger, F.A. et al., "Tumor size and lymph-node status in pancreatic carcinoma—is there a correlation to the preoperative immune function?," Langenbecks Archives of Surgery, vol. 384, pp. 473-478 (1999).

White, C.L. et al., "Intragastric beta-casomorphin(1-7) attenuates the suppression of fat intake by enterostatin," Peptides, vol. 21, pp. 1377-1381 (2000).

Winzell, M.S. et al., "Rat gastric procolipase: sequence, expression, and secretion during high-fat feeding," Gastroenterology, vol. 115, pp. 1179-1185 (1998).

Woltering, E.A. et al., "Development of a Novel in Vitro Human Tissue-Based Angiogenesis Assay to Evaluate the Effect of Antiangiogenic Drugs," Annals Surgery, vol. 237, pp. 790-800 (2003).

Wu, Y.D. et al., "Comparative study of enterostatin sequence in five rat strains and enterostatin bind proteins in rat and chicken serum," Peptides, vol. 23, pp. 537-544 (2002.

York, D.A. et al., "Brain amine responses to peripheral enterostatin," Int. J. Obes., vol. 18, p. 102 (1994) (Abs.).

York, D.A. et al., "Enterostatin as a regulator of fat intake," in Neural and metabolic control of macronutrient selection, H.R. Berthoud and R.J. Seeley (eds.), Chap 20, pp. 295-308, CRC Press (Boca Raton, USA) (2000).

York, D.A.et al., "Enterostatin: A peptide regulator of fat ingestion," in Pennington Symposium Series, Molecular Biology of Obesity, vol. 4, pp. 281-297 (G.A. Bray and D. Ryan, eds.), Louisiana State University Press, Baton Rouge USA (1996).

* cited by examiner

METHODS OF USING ENTEROSTATIN AS INHIBITOR OF ANGIOGENESIS

This is the United States national stage of international application PCT/US06/045528, filed 27 Nov. 2006, which claims the benefit of the 30 Nov. 2005 filing date of U.S. provisional application Ser. No. 60/741,500 under 35 U.S.C. §119(e).

The development of this invention was partially funded by the Government under a grant from the National Institutes of Health (NIDDK), grant no. DK45278. The Government has certain rights in this invention.

TECHNICAL FIELD

This invention pertains to a method to inhibit angiogenesis using a therapeutically effective amount of enterostatin.

BACKGROUND ART

Enterostatin

Enterostatin is the aminoterminal pentapeptide of procolipase that is released by proteolytic activity when procolipase is converted into colipase (9). The procolipase gene is expressed in the exocrine pancreas and the gastric and duodenal mucosa (25, 34, 53). In the gastric mucosa, the gene appears to be concentrated in enterochromaffin cells. More recently, procolipase and enterostatin were shown to be present in specific brain regions including the amygdala and hypothalamus (12).

Enterostatin Effects on Feeding Behavior. The peptide enterostatin has a dose-dependent and selective effect to inhibit fat intake in a number of dietary paradigms. The first criteria for establishing the physiological role of a peptide on feeding behavior is that it inhibits food or macronutrient intake in rats adapted to a three-choice macronutrient diet of fat, carbohydrate and protein (7, 36, 37). Enterostatin reduced intake of the fat macronutrient, but had no effect on either carbohydrate or protein intake. In a two-choice high-fat (HF) and low-fat (LF) diet paradigm experiment, enterostatin reduced only intake of the HF diet, but not of the LF diet (15) Similarly, enterostatin reduced intake of a single dietary source when the source was HF (17), but not when LF. The ability of enterostatin to selectively inhibit fat intake on a two- or three-choice feeding paradigm has been demonstrated after administration of enterostatin by either intraperitoneal, intracerebroventricular (icv), intraduodenal/intragastric, and near celiac arterial injection (15, 16, 19, 22, 27, 29, 52, 57). Similar to other gut peptides, enterostatin appeared to have at least two sites of action, one in the gastrointestinal tract and one in the central nervous system (20, 49, 57).

While the majority of the feeding studies with enterostatin have been performed in overnight fasted rats that have been previously adapted to the experimental diets, the selective effects towards dietary fat have been shown in free-feeding rats injected at the start of the dark cycle. The potency of enterostatin is reflected in the long duration of action on feeding, lasting up to six hours after a single injection in rats adapted to a six-hour feeding schedule, and lasting up to 24 hours after a single injection in rats adapted to ad-libitum feeding. Chronic icv administration of enterostatin from mini-osmotic pumps also attenuated the daily intake of dietary fat in rats fed either a single-choice HF diet or a two-choice HF/LF diet (15, 35). The decrease in daily food intake was accompanied by a reduction in fat deposition and body weight gain. However, in rats chronically treated with enterostatin and fed a low-fat diet for seven days, no significant reduction was seen in either energy intake or change in body weight gain. An intriguing characteristic of the response to enterostatin in both acute and chronic studies was that the reduction in intake of dietary fat is not compensated by an increase in the intake of other macronutrients when a dietary choice is available. This may result from a concomitant increase in corticotropin releasing hormone (CRH) secretion since enterostatin is known to activate the hypothalamic-pituitary-adrenal (HPA) axis (35).

Enterostatin has also been shown to reduce food intake in rabbits, sheep, and baboons (8, 30, 51). However, all of these studies were performed with single-choice diets. In humans, enterostatin administered by intravenous injection was found to reduce the subjective feeling of hunger (44), although was not found to reduce food intake (43).

Enterostatin effects on fat intake appear to be expressed at both gastrointestinal and central nervous system (CNS) sites. The response to peripherally-administered enterostatin was found to be mediated through the hepatic vagus nerve; the response was abolished by either selective hepatic vagotomy or capsaicin treatment (32, 49). Within the CNS, enterostatin was found to act on both the amygdala and paraventricular nucleus (PVN) (12, 14, 20). Enterostatin inhibited fat intake by way of a pathway that contained both serotonergic (55) and kappa-opioidergic (38) neurons. Kappa-opioidergic agonists inhibited the enterostatin effects on feeding, and a K-opioidergic antagonist or nor-Binaltorphamine (BNI) mimicked the effect of enterostatin on selective fat intake (1, 38). In contrast, the general serotonergic antagonist, metergoline but not a 5HT2 receptor antagonist, blocked the response to icy-administered enterostatin (57), and serotonin injections into the PVN inhibited dietary fat intake (10, 45).

A physiological regulator of feeding behavior must be effective at dose levels that are present in the animal. The in vivo concentration of enterostatin has not been established, due to problems in measuring enterostatin. Antibodies that are selective to enterostatin that could be used to analyze tissue levels of enterostatin have been difficult to find. The current values for enterostatin all appear very high, for example, plasma serum enterostatin of 5-40 nM in humans (4) and rats, cerebral spinal fluid enterostatin of 18-92 ng/ml, and brain enterostatin levels of 2.5 nmoles/g tissue (11). A suggestion of the existence of multiple forms of enterostatin in rats and in humans because of genetic polymorphisms in the enterostatin region of the procolipase parent molecule further complicates the efforts to measure enterostatin (11, 46). However, other data have disputed the suggestion of multiple forms (53, 54). Despite these measurement problems, enterostatin-like immunoreactivity has been shown to increase both in human serum and urine after a meal in a biphasic manner (4), and in lymph fluid of cats (50) and serum of rats after feeding (9).

Enterostatin regulation of insulin secretion. Several studies have shown that enterostatin inhibits insulin secretion (24, 26, 28, 39, 42, 47). In vivo perfusion of isolated islets and of the rat pancreas has been used to demonstrate that enterostatin directly inhibits insulin release from islet cells induced by either glucose, tolbutamide, or arginine. (39) Enterostatin ($10^{-9}$ to $10^{-5}$ M) inhibited insulin secretion from islets incubated in the presence of 16.7 mM glucose in a dose-dependent manner. Enterostatin also inhibited insulin secretion stimulated by glybenclamide (5.0 and 10 µM), phorbol 12-myristate-13-acetate (TPA) (50 and 100 nM), and the kappa-opioid agonist U50,488 (100 nM). The inhibitory effect of enterostatin on TPA-induced insulin secretion was attenuated, but still remained in the absence of extracellular $Ca^{2+}$. The enterostatin inhibition of insulin secretion was blocked by 8-Br-cAMP (1 mM), independent of extracellular $Ca^{2+}$. Enterostatin reduced the increase in intracellular cyclic AMP content produced by U50,488 (100 nM), in a manner parallel with changes in insulin release (42).

In vivo studies also have shown a reduction in insulin levels without any changes in plasma glucose suggesting an improvement in insulin sensitivity (15, 35). This occurred after both peripheral and central administration of enterostatin, reflecting both direct effects on the islet cells and indirect effects by way of a reduction in vagal stimulation to the pancreas.

Other Effects of Enterostatin. Enterostatin also been shown to affect gastrointestinal motility and gastric emptying (21, 40). The inhibition of gastric emptying was observed only after intracerebroventricular administration of enterostatin, but not after either intraperitoneal or intragastric administration, suggesting that enterostatin also affects efferent vagal activity. However, the inhibitory effect of enterostatin on consumption of a high fat diet was not related to the slow-down of gastric emptying (21). Enterostatin also had direct effects on pig intestine to prolong the quiescent phase I period of peristalsis, which slows down the absorption of nutrients and prolongs intestinal transit time. Enterostatin may also reduce cholesterol levels (48).

Enterostatin also has shown a number of autonomic and endocrine effects in addition to the effect on insulin secretion. It enhanced corticosterone secretion (35) and sympathetic stimulation to brown adipose tissue (32, 33), which would increase thermogenesis (41). These responses, in addition to the suppression of dietary fat intake, help explain the reduction in weight gain and body fat that was seen in rats treated chronically with either peripheral or central enterostatin (15, 35).

Circulating enterostatin. Enterostatin absorption across the intestine was found to be limited and slow, occurring mainly into lymphatic system. Detailed information of the changes in plasma enterostatin or brain uptake of enterostatin after a meal currently exist that would allow a temporal comparison with the termination of feeding and the development of satiety. The data that are available indicate the rise in plasma immunoreactive-like enterostatin activity is slow and does not peak until at least 60 minutes after feeding, which is inconsistent with a theory that an increase in circulating enterostatin plays a role in the termination of the immediate meal.

The presence of procolipase mRNA in the CNS together with enterostatin-like immunoreactivity has been demonstrated (12). Enterostatin also was found at high levels in the cerebrospinal fluid of rats. A hypothesis that this central system is important in determining the appetite for dietary fat is consistent with the evidence that endogenous production of enterostatin is reciprocally related to voluntary selection of fat across and within rat strains.

Enterostatin Receptors. Based on the areas responding to enterostatin, receptors would be expected to be located in brain, pancreas, and the gastrointestinal tract. Enterostatin has been shown not to bind to the galanin or Neuropeptide Y1 receptors (17), kappa-opioid receptors or cholecystokinin A receptors (13) Low affinity enterostatin binding was shown to a brain membrane preparation (Kd 230 nM) (56) and to SK-N-MC neuroepithelioma cells (Kd 40 nM) (2). The dose-response curve to enterostatin is biphasic, exhibiting an inhibition of food intake at lower doses, but stimulation of food intake at higher doses (22). However, since enterostatin has been shown to be biologically active on food intake at extremely low doses compared to other peptides and to inhibit insulin secretion from isolated pancreatic islets at doses of $10^{-10}$ to $10^{-6}$M, a proposed low affinity casomorphin binding site probably is not the biologically important enterostatin receptor that inhibits fat intake and insulin secretion. More recently the beta subunit of ATP synthase has been identified as an enterostatin receptor. The initial suggestion came from affinity chromatography studies (59). Subsequently, it has been shown that enterostatin and its antagonist beta-casomorphin bind to this purified protein, that binding can be associated with biological activity across a range of analogs, and that this protein is present in the plasma membranes of tissues that are responsive to enterostatin (amygdala, pancreas, liver). (60)

Angiogenesis

In an adult, two types of blood vessels can potentially be found. The normal blood vessel is a resting, quiescent, fully developed vessel. A second form, a proliferating or developing blood vessel, occurs rarely during the normal life cycle (only in early development and reproduction, e.g., menstrual cycle and pregnancy). In contrast, the process of angiogenesis, the proliferation and development of new blood vessels, often occurs in wound healing and in pathological processes, e.g., tumor growth. Angiogenesis is a complex process involving many stages, including extracellular matrix remodeling, endothelial cell migration and proliferation capillary differentiation, and anastomosis. All detectable solid tumors (tumors over 2 mm in diameter) exploit angiogenesis to supply the needed blood to proliferating tumor cells. Studies have demonstrated that the level of vascularization in a tumor is strongly associated with metastasis in melanoma, breast, and lung carcinomas. See R. Bicknell, "Vascular targeting and the inhibition of angiogenesis," Annals of Oncology, vol. 5, pp. 45-50 (1994).

Angiogenesis inhibitors have been suggested to intervene into neoplastic processes. See G. Gasparini, "The rationale and future potential of angiogenesis inhibitors in neoplasia," Drugs, vol. 58, pp. 17-38 (1999). The inhibitory agents block angiogenesis, thereby causing tumor regression in various types of neoplasia. Known therapeutic candidates include naturally occurring angiogenic inhibitors (e.g., angiostatin, endostatin, platelet factor-4, somatostatin and its analogs), specific inhibitors of endothelial cell growth (e.g., TNP-470, thalidomide, interleukin-12), agents that neutralize angiogenic molecules (e.g., antibodies to fibroblast growth factor or vascular endothelial growth factor), suramin and its analogs, tecogalan, agents that neutralize receptors for angiogenic factors, agents that interfere with vascular basement membrane and extracellular matrix (e.g., metalloprotease inhibitors, angiostatic steroids), and anti-adhesion molecules (e.g., antibodies such as anti-integrin alpha v beta 3). See L. Rosen, "Antiangiogenic strategies and agents in clinical trials," Oncologist, vol. 5, supplement 1, pp. 20-27 (2000).

Abnormal angiogenesis occurs when improper control of angiogenesis causes either excessive or insufficient blood vessel growth. Excessive blood vessel proliferation favors tumor growth and development of distant metastases, blindness, skin disorders such as psoriasis, and rheumatoid arthritis. Diseases or conditions that have been associated with undesired vascularization include, for example, diabetic retinopathy, retinopathy of prematurity, corneal graft rejection, neovascular glaucoma, retrolental fibroplasia, epidemic keratoconjunctivits, Vitamin A deficiency, atopic keratitis, contact lens overwear, superior limbic keratitis, pterygium keratitis sicca, Sjogren's syndrome, acne rosacea, phylectenulosis, syphilis, myobacterial infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, radial keratotomy, macular degeneration, sickle cell anemia, sarcoidosis, pseudoxanthoma elasticum, Paget's disease, vein occlusion, carotid obstructive disease, chronic uveitis, chronic vitritis, Lyme's disease, Eales' disease, Behcet's disease, myopia, optic pits, Stargardt's disease, pars planitis, chronic retinal detachment, hyperviscosity syndromes, toxoplasmosis, post-laser complications, abnormal proliferation of fibrovascular or fibrous tissue, hemangiomas, Osler-Weber-Rendu disease, solid tumors, blood borne tumors, acquired immune deficiency syndrome, ocular neovascular disease, age-related macular degeneration, osteoarthritis, diseases caused by chronic inflammation, Crohn's disease, ulcerative colitis, tumors of rhabdomyosarcoma, tumors of retinoblastoma, tumors of Ewing's sarcoma, tumors of neuroblastoma, tumors of ostteosarcoma, leukemia, psoriasis, atherosclerosis, pemphigoid, infections causing retinitis or choroiditis, presumed ocular histoplasmosis, Best's disease, proliferative vitreoretinopathy, Bartonellosis, acoustin neuroma, neurofibroma, trachoma, pyogenic granulomas, obesity, corneal neovascularization, malignant tumor growth beyond 2 mm, benign tumors, benign functional endocrine tumors, arterial/venous malformations, primary hyperparathyroidism, secondary hyperparathyroidism, and tertiary hyperparathyroidism. Other angiogenic-related diseases may include, for example, diseases associated with rubeosis (neovascularization of the angle), and diseases caused by abnormal proliferation of fibrovascular or fibrous tissue, including all forms of proliferative vitreoretinopathy. Any disease having a known angiogenic counterpart could potentially be treated with an anti-angiogenic factor, e.g., psoriasis. See D. Creamer et al., "Overexpression of the angiogenic factor platelet-derived endothelial cell growth factor/thymidine phosphorylase in psoriatic epidermis," Br. J. Dermatol., vol. 137, pp. 851-855 (1997).

Angiogenesis is a prominent contributor to solid tumor growth and the formation of distant metastases. Several experimental studies have concluded that primary tumor growth, tumor invasiveness, and metastasis all require neovascularization. The process of tumor growth and metastasis is complex, involving interactions among transformed neoplastic cells, resident tissue cells (e.g., fibroblasts, macrophages, and endothelial cells), and recruited circulating cells (e.g., platelets, neutrophils, monocytes, and lymphocytes). A possible mechanism for the maintenance of tumor growth is an imbalance, or disregulation, of stimulatory and inhibitory growth factors in and around the tumor. Disregulation of multiple systems allows the perpetuation of tumor growth and eventual metastasis. Angiogenesis is one of many systems that is disregulated in tumor growth. In the past it has been difficult to distinguish between disregulation of angiogenesis and disregulation of other systems affecting a developing tumor. Another complicating factor is that aggressive human melanomas mimic vasculogenesis by producing channels of patterned networks of interconnected loops of extracellular matrix, in which red blood cells, but not endothelial cells, are detected. See A. J. Maniotis et al., "Vascular channel formation by human melanoma cells in vivo and in vitro: Vasculogenic mimicry," Am. J. Pathol., vol. 155, pp. 739-52 (1999). These channels may facilitate perfusion of tumors, independent of perfusion from angiogenesis.

A tumor cannot expand beyond approximately 2 mm without a blood supply to provide nutrients and remove cellular wastes. Tumors in which angiogenesis is important include solid tumors, and benign tumors including acoustic neuroma, neurofibroma, trachoma, and pyogenic granulomas. Inhibiting angiogenesis could halt the growth and potentially lead to regression of these tumors. Angiogenic factors have been reported as being associated with several solid tumors, including rhabdomyosarcoma, retinoblastoma, Ewing sarcoma, neuroblastoma, and osteosarcoma.

Angiogenesis has also been associated with some non-solid tumors, including blood-born tumors such as leukemia, various acute or chronic neoplastic diseases of the bone marrow marked by unrestrained proliferation of white blood cells, usually accompanied by anemia, impaired blood clotting, and enlargement of the lymph nodes, liver, and spleen. It is believed that angiogenesis may play a role in the abnormalities in the bone marrow that give rise to leukemias and multiple myelomas.

Anti-angiogenic factors inhibit tumor growth beyond 2 mm by inhibiting the angiogenic response and thus inhibiting blood vessel growth to the tumor. Although angiogenesis in a tumor may begin at an early stage, a tumor requires a blood supply to grow much beyond about 2 mm. Up to 2 mm diameter, tumors can survive by obtaining nutrients and oxygen by simple diffusion. Most anti-angiogenic factors are not cytotoxic, i.e., capable of killing the tumor cells directly. Small tumors of a size about 1 $mm^3$ can be effectively inhibited and destroyed by factors, either endogenous or exogenous, that stimulate the immune system. It is generally accepted that once a tumor has reached a critical size, the immunological system is no longer able to effectively destroy the tumor; i.e., there is a negative correlation between tumor size and immune competence. See A. K. Eerola et al., "Tumour infiltrating lymphocytes in relation to tumour angiogenesis, apoptosis," Lung Cancer, vol. 26, pp. 73-83 (1999); and F. A. Wenger et al., "Tumor size and lymph-node status in pancreatic carcinoma—is there a correlation to the preoperative immune function?," Langenbecks Archives of Surgery, vol. 384, pp. 473-478 (1999). Early adjuvant use of an effective anti-angiogenic agent to preclude development of tumor metastases beyond 1 to 2 $mm^3$ may allow more effective tumor attack and control by the body's immunological mechanisms. In addition, prolonged adjuvant use of a non-toxic angiogenic inhibitor may prevent tumor dissemination by blocking the growth of vessels required for the transport of tumor cells that would form metastatic foci.

Angiogenesis has also been implicated in obesity. Several mice strains, both young and aged animals, used as obesity models treated with anti-angiogenic agents lost weight. See M. A. Rupnick et al., "Adipose tissue mass can be regulated through the vasculature," PNAS, vol. 99, pp. 10730-10735 (2002). This same study also found that adipose tissue mass was reduced by the anti-angiogenic compounds.

New anti-angiogenic factors are needed, in particular, compounds that not only inhibit new angiogenic growth, but also that degrade existing capillary networks. Very few anti-angiogenic factors have been reported to diminish existing capillary networks.

DISCLOSURE OF INVENTION

We have discovered that enterostatin inhibits angiogenesis in an in vitro adipose tissue angiogenesis model. In concentrations from about $10^{-6}$ to about $10^{-9}$ M, enterostatin effectively blocked the angiogenic response. Enterostatin will be effective in treating non-cancerous and cancerous diseases that involve an increase in angiogenesis, e.g., rheumatoid arthritis, retinopathy of prematurity, neovascular glaucoma, diabetic retinopathy, and psoriasis. This antiangiogenic activity was confirmed in two additional tissue cells lines (liver and neuronal cells) using a microarray analysis.

MODES FOR CARRYING OUT THE INVENTION

We have previously shown that enterostatin binds to the beta subunit of ATP synthase when the receptor is located in the plasma membrane. See M. Park et al., "The F(1)-ATPase beta-subunit is the putative enterostatin receptor," Peptides, vol. 25, pp. 2127-2133 (2004). We now have shown that enterostatin is a potent inhibitor of angiogenesis, and thus would be useful in many diseases that are based on pathological angiogenesis.

EXAMPLE 1

Enterostatin Inhibits Angiogenesis
Angiogenesis Assay.
Tissue Preparation: Discarded fat from human surgery was cut into fragments approximately 1 mm thick and 2 mm in diameter. These fat fragments were placed in 96-well plates loaded with human thrombin solution (0.05 IU in 40 µL double distilled water/well). The fat fragments were placed in the prepared 96-well plates and covered with 100 µl clotting media. The clotting media consisted of fibrinogen (3 mg/ml) (Sigma Chemical Co., St. Louis, Mo.) and ε-amino caproic acid (0.5%) (Sigma Chemical Co., St. Louis, Mo.) in human placental vein angiogenesis model (HPVAM) media. HPVAM media consists of Medium 199 (GibcoBRL, Gaithersburg, Md.), and antibiotic/antimycotic solution (100 U penicillin, 100 U streptomycin sulfate and 2.5 µg/ml amphotericin beta) (GibcoBRL, Gaithersburg, Md.). The mixture was allowed to clot by incubation in 6% $CO_2$, 94% air at 37° C. in a humidified incubator. After the media had gelled overnight, the fat-containing clot was supplemented with 1 mL HPVAM media containing 20% fetal bovine serum (GibcoBRL, Gaithersburg, Md.). The total volume of each well was 2 mL.

Angiogenic Evaluation: All wells were evaluated for angiogenic sprouting by examination at 40× and 200× magnification by an unbiased observer using an inverted microscope. Angiogenesis was defined by two criteria. First, the number of wells (as a percentage of the total plated) that developed new vessel growth was termed initiation. This was defined by the presence of at least three angiogenic sprouts of approximately 0.5 mm in length growing from the periphery of the fat tissue. The degree of angiogenic response was assessed using a semi-quantitative visual rating scale as described in E. A. Woltering et al., "Development of a novel in vitro human tissue-based angiogenesis assay to evaluate the effect of antiangiogenic drugs," Ann. Surg., vol. 237, pp. 790-798 (2003). The tissue was visually divided into four quadrants. Each quadrant was given a numeric score from 0-4 based on the length and density of the new vessel growth, and on the percentage of the quadrant's circumference involved with the angiogenic response. Numeric results from the four quadrants were summed and expressed as an angiogenic index (AI, 1-16). This rating scale has been validated using multiple independent observers as described in C. Hornick et al., "Inhibition of angiogenic initiation and disruption of newly established human vascular networks by juice of *Morinda citrifola* (Noni)," Angiogenesis, vol. 6, pp. 143-149 (2004).

Electron Microscopy and Histology. After 15 days in culture, the clots were removed and fixed in 2% glutaraldehyde and 0.1 M cacodylate buffer with 3% sucrose for 2 hours. The clots were rinsed 5 times with 0.1 M buffer containing 3% sucrose and glycine 0.02 M overnight. The clots were then post-fixed with 2% osmium tetraoxide for 1 hour, rinsed with water, and en bloc stained with 0.5% uranyl acetate for 1 hour in the dark. They were then dehydrated with ethanol series overnight, infiltrated with 1:1 ethanol:LR white resin for 3 hours, and in 100% LR white resin overnight. Finally, the clots were embedded at 60° C. overnight, sectioned, stained with Reynolds lead citrate, and imaged with a JEOL transmission electron microscope at 100 CX.

Florescent light micrographs were taken of DAPI-stained live cells with a Nikon microphot and SPOT RT digital camera. The DAPI blue dye stained and identified nuclei. Images of the clot were taken through a dissecting scope with a Leica MZ7 and a SPOT Insight digital camera.

Figure 1A:
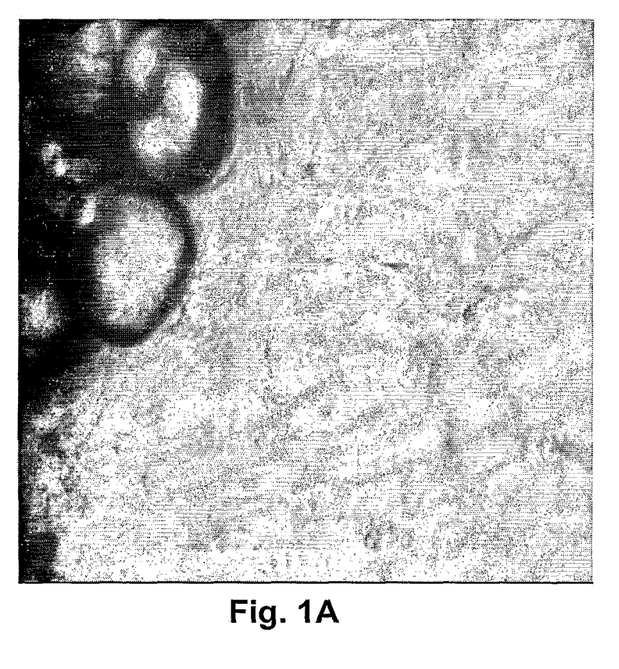
FIG. 1A illustrates a photomicrograph of adipose tissue incubated without the addition of enterostatin.
Figure 1B:
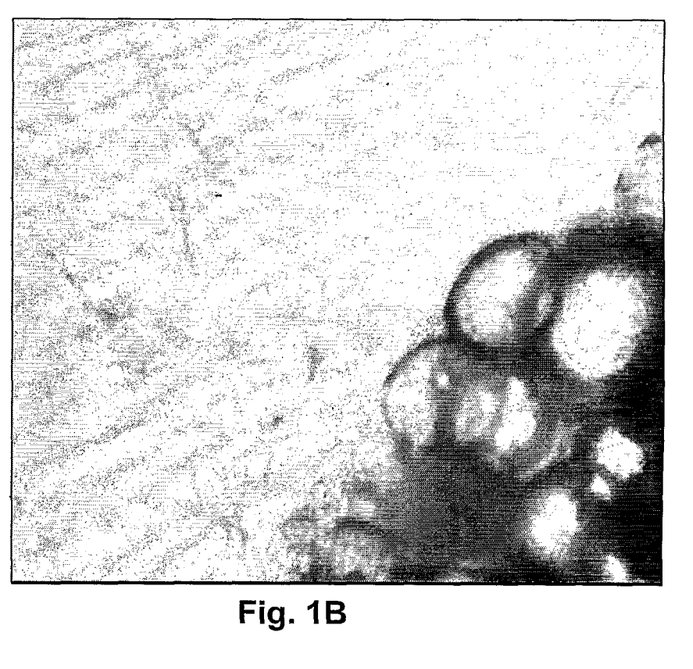
FIG. 1B illustrates a photomicrograph of adipose tissue incubated in the presence of $10^9$ molar enterostatin.

FIGS. 1A and 1B are photomicrographs of the adipose tissue incubated without enterostatin (FIG. 1A) and with $10^{-9}$ M enterostatin. The tissue incubated with enterostatin can clearly be seen to have fewer new blood vessels than the control tissue.

Figure 2:
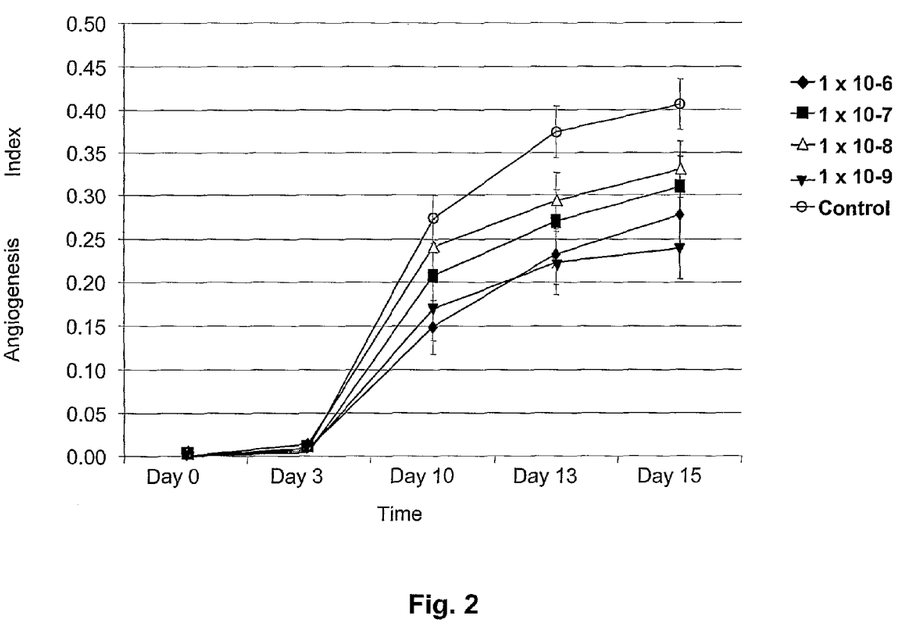
FIG. 2 illustrates a dose-response curve using various concentrations of enterostatin (range of $10^{-9}$ to $10^{-6}$M) to measure effect of each on the angiogenic index.
Figure 3:
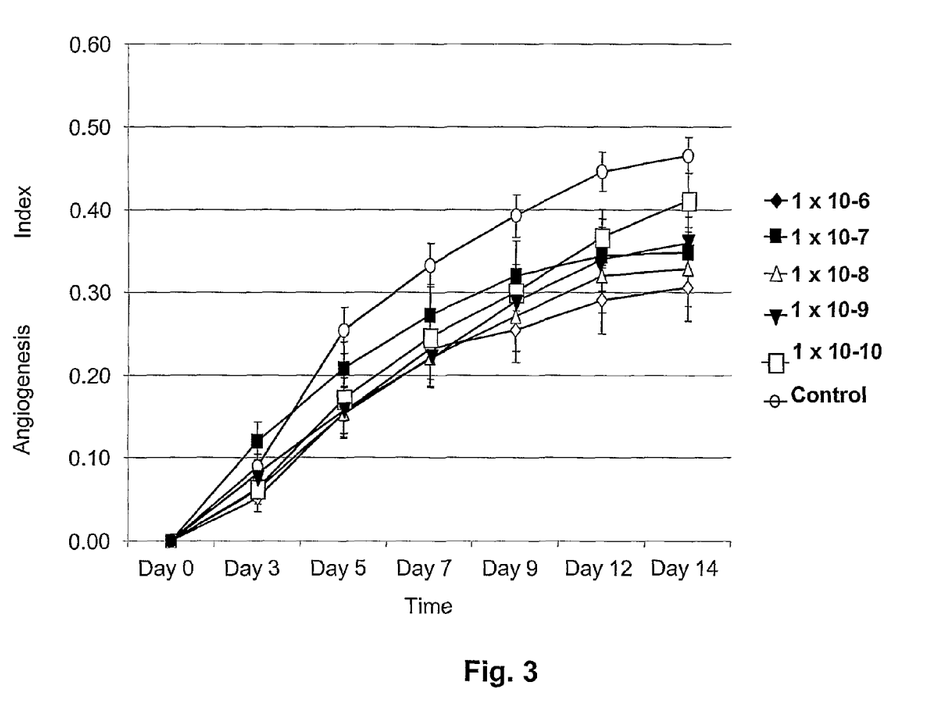
FIG. 3 illustrates a dose-response curve using various concentrations of enterostatin (range of $10^{-1}$ to $10^{-6}$M) to measure effect of each on the angiogenic index.

FIGS. 2 and 3 represent two separate dose-response experiments that indicated the effect of various concentrations of enterostatin on the angiogenic index. As shown in FIG. 2, enterostatin showed a dose dependent inhibition from the range of $10^{-8}$ to $10^{-6}$ M. However, the greatest inhibition at day 15 was $10^{-9}$ M, indicating a U-shaped dose response curve. FIG. 3 indicates that $10^{-10}$ M enterostatin was the least inhibitory of angiogenesis as measured by the angiogenic index.

Figure 4:
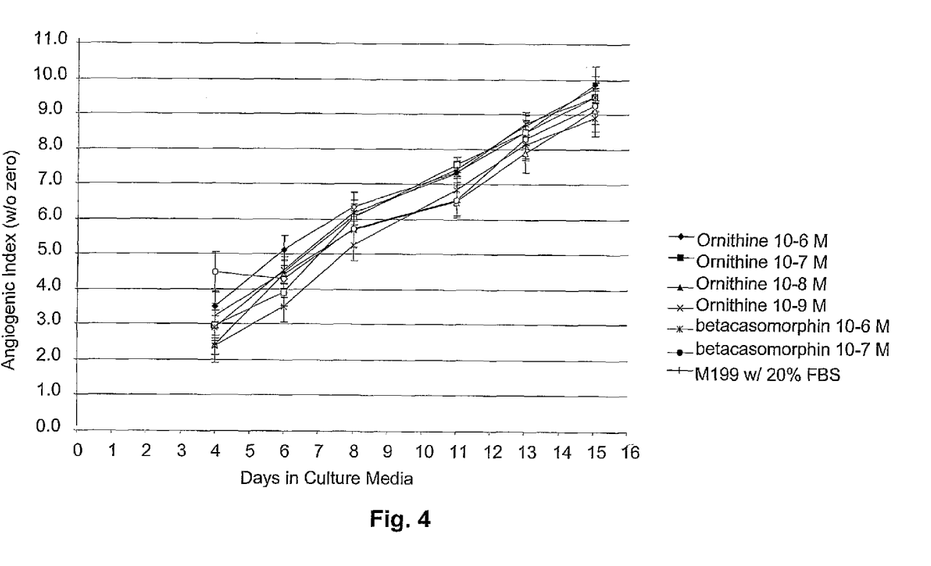
FIG. 4 illustrates the lack of an inhibitory effect on the angiogenic index when using an enterostatin antagonist (β-casomorphin1-7) and a enterostatin metabolite (APGP-ornithine).

Finally, using the same angiogenesis model, the effects of the enterostatin antagonist, 13-casomorphin 1-7, were investigated using concentrations of $10^{-6}$ and $10^{-7}$ M. As shown in FIG. 4, this antagonist had no effect on angiogenesis. In addition, a metabolite of enterostatin, APGP-ornithine, was tested in concentrations from $10^{-6}$ to $10^{-9}$ M. Again, as shown in FIG. 4, none of these concentrations of the metabolite inhibited angiogenesis. Since this metabolite was shown to affect food intake in rats, the angiogenic response to enterostatin may be mediated through a different receptor or signaling pathway than the food intake response to enterostatin.

Figure 5:
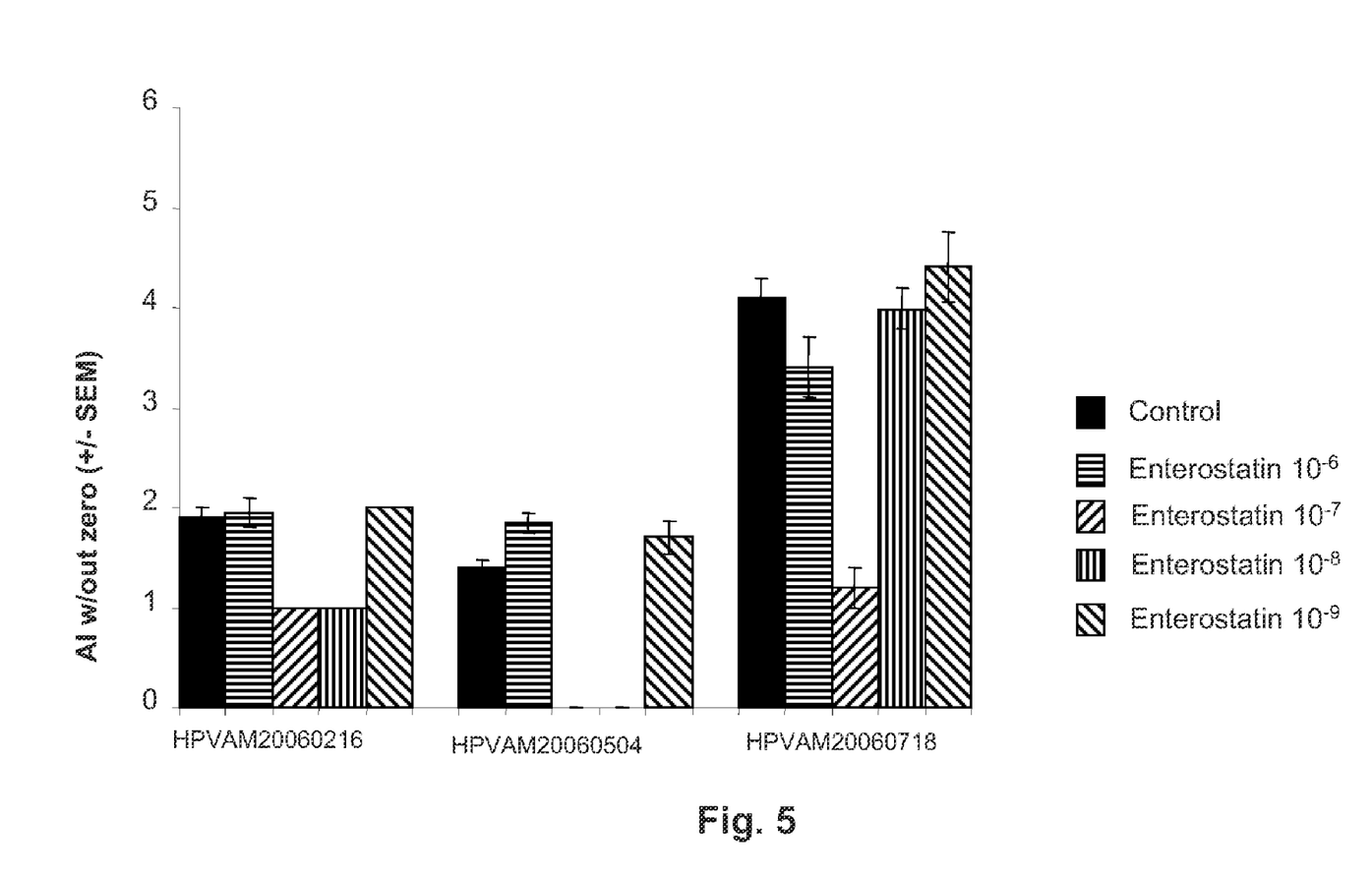
FIG. 5 illustrates the dose-related effects of enterostatin on angiogenesis in the human umbilical vein model.

In addition, another angiogenesis model was tried, the human umbilical vein model as described by Woltering et al. (61). This model uses discarded umbilical veins to assay the effect of various compounds on angiogenesis. As shown in FIG. 5, the effect of various concentrations of enterostatin on this model showed a similar U-shaped dose response as seen in the adipocyte model. Thus enterostatin was effective in inhibiting angiogenesis in these two tissue types.

EXAMPLE 2

Microarray Gene Analysis

HepG2 cells (a human liver carcinoma cell line) and GT1-7 cells (a neuronal cell line) were cultured by standard procedures and incubated with varying concentrations of enterostatin for 60 minutes. At the completion of the incubation period, cells were lysed, recovered from the plates, and extracted for RNA using TRI REAGENT® (Molecular Research Center, Inc, Cincinnati, Ohio). The RNA was then purified using the RNeasy® Mini Kit (Qiagen, Valencia, Calif.). RNA quality was visually assessed using agarose gel electrophoresis and quantified by UV spectrophotometric analysis ($A_{260}$ and $A_{280}$ nm). All RNA had $A_{260}/A_{280}$ ratios greater than 1.75 and less than 2.10. RNA integrity was checked using an RNA 6000 nano lab chip kit (Agilent Technologies, Foster City, Calif.).

The high density microarrays used in this study were generated by the Genomics Core Microarray Facility at the Pennington Biomedical Research Center using a Gene Machines OmniGrid Microarrayer (San Carlos, Calif.) to spot 70-mer oligonucleotides (mouse library versions 1.0 and 2.0, Operon Biotechnologies, Inc., Huntsville, Ala.) onto poly-lysine-coated glass microscope slides. The mouse libraries used for printing slides represent over 19,000 well-characterized genes; information concerning gene specifics can be located on the Operon website.

An equal amount (6 μg) of total RNA from each of the enterostatin doses and the control (untreated) cells was subjected to reverse transcription with oligo(dT), labeled with Cy3 and Cy5 dyes using the Micromax TSA™ Labeling and Detection Kit protocol (Perkin Elmer Life Sciences, Inc., Boston, Mass.) and hybridized to in-house spotted slides. The TSA™ labeling method uses a tyramide signal amplification process, and is highly sensitive, allowing for the use of very small amounts (as little as 2 μg) of total RNA with consistent and reproducible signal amplification across arrays. cDNA from enterostatin treated groups (0.01, 0.1 and 1.0 uM enterostatin) were labeled with Cy5 and hybridized against control cDNA labeled with Cy3. Control-Cy5 labeled cDNA was also compared to control Cy3 cDNA.

Slides were scanned using a GSI Lumonics ScanArray 5000 laser scanner (Perkin Elmer Life Sciences, Inc., Boston, Mass.) at a relatively low and a relatively high laser intensity and expression data was analyzed using the QuantArray V3.0 software package (Perkin Elmer Life Sciences, Inc.). The data were then normalized using a subarray-by-subarray LOWESS (Locally Weighted Regression and Scatterplot Smoothing) statistical algorithm developed in house at the Pennington Biomedical Research Center. Using this system, genes were identified that were up or down regulated by at least 1.7× and showed a dose-response relationship to enterostatin. The data was then subjected to pathway analysis using the Panther software (Applied Biosystems, Foster City, Calif.), and this identified genes associated with angiogenesis that were regulated in response to enterostatin.

RT PCR. Microarray data was confirmed by semiquantitative RT PCR using forward and reverse primers (Fisher Life Sciences or Invitrogen Life Technologies, Carlsbad, Calif.) designed wherever possible to span both the exon-exon splice sites and the region of the gene sequence corresponding to the location of the 70-mer oligonucleotide on the microarray.

Genomic effects of enterostatin. Microarray analysis identified 22 genes related to the angiogenesis pathway that were upregulaed or downregulated by enterostatin (Table 1) in the HepG2 and GT1-7 cells. Confirmation of these changes by RTPCR will be done. These gene expression data provide substantive support for the physiological observations on angiogenesis in the fat depot model and suggest that enterostatin may play an important role in the regulation of angiogenesis.

TABLE 1

Angiogenesis genes responsive to enterostatin in GT1-7 AND HepG2 cells.

| GENE ID | GENE NAME |
|---|---|
| 29857 | mitogen-activated protein kinase 12(Mapk12) |
| 18762 | protein kinase C, zeta (Prkcz) |
| 20379 | secreted frizzled-related sequence protein 4 (Sfrp4) |
| 13542 | Dishevelled, dsh homolog 1 (*Drosophila*) (Dvl1) |
| 18479 | p21 (CDKN1A)-activated kinase 1 (Pak1) |
| 19668 | Recombining binding protein suppressor of hairless-like (*Drosophila*) (Rbpsuhl) |
| 21415 | Transcription factor 3 (Tcf3) |
| 13842 | Eph receptor A8 (Epha8) |
| 15170 | Hemopoietic cell phosphatase (Hcph) |
| 18706 | Phosphatidylinositol 3-kinase, catalytic, alpha polypeptide (Pik3ca) |
| 224860 | Phospholipase C-like 2 (Plcl2) |
| 14281 | FBJ osteosarcoma oncogene (Fos) |
| 57265 | Frizzled homolog 2 (*Drosophila*) (Fzd2) |
| 26420 | Mitogen activated protein kinase 9 (Mapk9) |
| 26416 | Mitogen activated protein kinase 14 (Mapk14) |
| 26415 | Mitogen activated protein kinase 13 (Mapk13) |
| 110157 | v-raf-1 leukemia viral oncogene 1 (Raf1) |
| 14183 | Fibroblast growth factor receptor-related (ptk group xv) (Fgfr2) |
| 14186 | Fibroblast growth factor receptor 4 (Fgfr4) |
| 143679 | Frizzled homolog 5 (*Drosophila*) (Fzd5) |
| 57265 | Frizzled homolog 2 (*Drosophila*) (Fzd2) |
| 26401 | Mitogen activated protein kinase kinase kinase 1 (Map3k1) |
| 22339 | Vascular endothelial growth factor A (Vegfa) |

Miscellaneous

The term "enterostatin" used herein and in the claims refers to the peptide enterostatin, its derivatives and analogs. The terms "derivatives" and "analogs" are understood to be compounds that are similar in structure to enterostatin and that exhibit a qualitatively similar effect on angiogenesis as does the unmodified enterostatin. Examples of such derivatives and analogs are well known and are described in Table 1 found in M. Park et al., "The F(1)-ATPase beta-subunit is the putative enterostatin receptor," Peptides, vol. 25, pp. 2127-2133 (2004).

The term "enterostatin agonist" as used herein refers to a molecule that selectively inhibits angiogenesis by binding to the $F_1$-ATPase (3-subunit in the plasma membrane or an alternative enterostatin receptor in the plasma membrane. As used herein, enterostatin agonist can include mimetics of enterostatin. An enterostatin agonist can also act, for example, by increasing the binding ability of enterostatin, or by favorably altering the conformation of the enterostatin receptor.

The term "enterostatin antagonist" as used herein refers to a compound that selectively inhibits or decreases the translocation of the $F_1$-ATPase β-subunit into the plasma membrane in tissues in which enterostatin would increase the translocation. An antagonist can act by any antagonistic mechanism, such as by binding to enterostatin or to $F_1$-ATPase β-subunit or an alternative enterostatin receptor, thereby inhibiting binding between enterostatin and the $F_1$-ATPase β-subunit or the alternative enterostatin receptor. An enterostatin antagonist can also act indirectly, for example, by modifying or altering the native conformation of either enterostatin or $F_1$-ATPase β-subunit.

The term "therapeutically effective amount" as used herein refers to an amount of enterostatin or its agonists sufficient to either inhibit angiogenesis or to degrade existing capillary networks to a statistically significant degree (p<0.05). The term "therapeutically effective amount" therefore includes, for example, an amount sufficient to prevent the growth of angiogenic vessels found in diseases that include tumor growth, diabetic retinopathy, psoriasis, retinopathy of prematurity, and preferably to reduce by at least 50%, and more preferably to reduce by at least 90%, the amount of angiogenesis. The dosage ranges for the administration of enterostatin are those that produce the desired effect. Generally, the dosage will vary with the age, weight, condition, sex of the patient, type of tumor, the degree of tumor development, and the degree of angiogenic response. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the extent of angiogenic inhibition or remission by methods well known to those in the field. Moreover, enterostatin can be applied in pharmaceutically acceptable carriers known in the art. The application can be oral, by injection, or topical.

The present invention provides a method of preventing, treating, or ameliorating a disease that causes an angiogenic response in the body such as tumors, retinopathy, and psoriasis, comprising administering to a subject at risk for a disease or displaying symptoms for such disease, a therapeutically effective amount of enterostatin or its agonists. The term "ameliorate" refers to a decrease or lessening of the symptoms or signs of the disorder being treated. The symptoms or signs that may be ameliorated include those associated with an increase in angiogenesis in the body.

References
1. Barton C., L. Lin, D. A. York and G. A. Bray. Differential effects of enterostatin, galanin and opioids on high-fat diet consumption. *Brain Res.* 702:55-60, 1995
2. Berger K, Sivars U, Winzell M S, Johansson P, Hellman U, Rippe C, and Erlanson-Albertsson C. Mitochondrial ATP synthase—a possible target protein in the regulation of energy metabolism in vitro and in vivo. *Nutr Neurosci* 2002; 5: 201-210.
3. Berger K, Winzell M S, Erlanson-Albertsson C. Binding of enterostatin to the human neuroepithelioma cell line SK-N-MC. *Peptides* 19: 1525-1531, 1998.
4. Bowyer, R. C., Rowston, W. M., Jehanli, A. M. T., Lacey, J. H., Hermon-Taylor, J., The effect of a satiating meal on the concentrations of procolipase activation peptide in the serum and urine of normal and morbidly obese individuals, *Gut.*, 34, 1520-1525, 1993.
5. Chang S, Park S, Kim S and Kang C. Interaction of the C-terminal domain of p43 and the α-subunit of ATP synthase: its functional implication in endothelial cell proliferation. *J. Biol. Chem.* 277; 8388-8394, 2001.
6. Das B, Mondrogan M. O., Sadeghian M, Hatcher V B and Norin A J. A novel ligand in lymphocyte mediated cytotoxicity: expression of beta subunit of H+ transporting ATP synthase on the surface of tumor cell lines. *J. Exp. Med.* 180: 273-81, 1994
7. Erlanson-Albertsson, C., Jie, M., Okada, S., York, D., Bray, G. A., Pancreatic procolipase propeptide, enterostatin, specifically inhibits fat intake, *Physiol. Behav.*, 49, 1191-1194, 1991.
8. Erlanson-Albertsson, C., Larsson, A., A possible physiological function of procolipase activation peptide in appetite regulation, *Biochimie*, 70, 1245-1250, 1988.
9. Erlanson-Albertsson, C., York, D., Enterostatin—A peptide regulating fat intake, *Obesity Res*, 5, 360-372, 1997.
10. Halford J, Smith B K, Blundell J. Serotonin (5HT) and serotonin receptors in the regulation of macronutrient intake In: Neural and Metabolic Control of Macronutrient intake eds H R Berthoud and R J Seeley, pp 425-446 CRC Press, Boca Raton. 2000.
11. Imamura, M., Sumar, N., Hermon-Taylor, J., Robertson, H. J. F., Prasad, C., Distribution and characterization of enterostatin-like immunoreactivity in human cerebrospinal fluid. *Peptides*, 19: 1385-91, 1998.
12. Lin L, Braymer HD and York DA. Procolipase gene and enterostatin expression in the rat brain. *FASEB J;* 2002; A783.
13. Lin L, S. R. Thomas, G. Kilroy, G. J. Schwartz and D. A. York. The enterostatin inhibition of dietary fat intake is dependent upon CCKA receptors. *Am. J. Physiology* August; 285(2): R321-8, 2003.
14. Lin L., D. A. York. Amygdala enterostatin induces c-Fos expression in regions of hypothalamus that innervate the PVN. *Brain Res.* 2004 Sep. 10; 1020(1-2):147-53.
15. Lin, L., Chen, J., York, D. A., Chronic icy enterostatin preferentially reduced fat intake and lowered body weight, *Peptides*, 18, 657-661, 1997.
16. Lin, L., G. Bray, and D. A. York. Enterostatin suppresses food intake in rats after near celiac and intracarotid arterial injection. *Am. J. Physiol. Reg Integr Comp Physiol.* 2000 May; 278(5):R1346-51.
17. Lin, L., Gehlert, D. R., York, D. A., Bray, G. A., Effect of enterostatin on the feeding responses to galanin and NPY, *Obes. Res.*, 1, 186-192, 1993.
18. Lin, L., Umahara, M. York, D. A., Bray, G. A., β-casomorphins stimulate and enterostatin inhibits the intake of dietary fat in rats. *Peptides*, 19, 325-331, 1998.
19. Lin, L., York, D. A., Enterostatin actions in the amygdala and PVN to suppress feeding in the rat, *Peptides*, 18, 1341-1347, 1997.
20. Lin, L., York, D. A., Changes in the microstructure of feeding after administration of enterostatin into the paraventricular nucleus and the amygdala, *Peptides*, 19, 557-562, 1998.
21. Lin, L., York, D. A., Comparisons of the effects of enterostatin on food intake and gastric emptying in rats, *Brain Res*, 745, 205-209, 1997.
22. Lin, L., Okada, S., York, D. A., Bray, G. A., Structural requirements for the biological activity of enterostatin, *Peptides*, 15, 849-854, 1994
23. Martinez L O, Jacquet S, Esteve J P, Rolland C, Cabezon E, Champagne E, Pineau T, Georgeaud V, Walker J E, Terce F, Collet X, Perret B, and Barbaras R. Ectopic beta-chain of ATP synthase is an apolipoprotein A-I receptor in hepatic HDL endocytosis. *Nature* (Lond) 2003; 421: 75-79.
24. Mei J, Bourras M, Erlanson-Albertsson C. Inhibition of insulin by intraduodenally infused VPDPR in rats. *Peptides* 18: 651-657, 1997
25. Mei, S., Bowyer, R. C., Jehanli, A. M. T., Patel, G., Erlanson-Albertsson, C., Identification of enterostatin, the pancreatic procolipase activation peptide, in the intestine of rat: effect of CCK-8 and high-fat feeding, *Pancreas*, 8, 488-493, 1993.
26. Mei, J., Cheng, Y., Erlanson-Albertsson, C., Enterostatin—its ability to inhibit insulin secretion and to decrease high-fat food intake, *Int. J. Obesity*, 17, 701-704, 1993.
27. Mei, J., Erlanson-Albertsson, C., Effect of enterostatin given intravenously and intracerebroventricularly on high-fat feeding in rats, *Regul. Pept.*, 41, 209-218, 1992

28. Mei, J., Erlanson-Albertsson, C., Plasma insulin response to enterostatin and effect of adrenalectomy in rat, *Obes. Res.,* 4, 513-519, 1996.
29. Mei, J., Erlanson-Albertsson, C., Role of intraduodenally administered enterostatin in rat: inhibition of food intake, *Obes. Res.,* 4, 161-165, 1996.
30. Miner, J. L., Erlanson-Albertsson, C., Paterson, J. A., Baile, C. A., Reduction of feed intake in sheep by enterostatin, the procolipase activation peptide, *J. Alin. Sci.,* 72, 1578-1582, 1994.
31. Moser t ET AL Angiostatin binds ATP synthase on the surface of human endothelial cells. *Proc. Natl. Acad. Sci.* 96: 2811-2816, 1999
32. Nagase H, A. Nakajimia, H. Sekihara, D. A. York and G. A. Bray. Regulation of feeding behavior, gastric emptying, and sympathetic nerve activity to interscapular brown adipose tissue by galanin and enterostatin: the involvement of vagal-central nervous system interactions. *J. Gastroenterol.* November; 37 Suppl 14:118-27, 2002.
33. Nagase H., G. A. Bray and D. A. York. Effect of galanin and enterostatin on sympathetic nerve activity to interscapular brown adipose tissue. *Brain Res.* 709:44-50, 1996.
34. Okada S., D. A. York and G. A. Bray. Procolipase mRNA: Tissue localization and effects of diet and adrenalectomy. Biochem. J. 292:787-789, 1993
35. Okada, S., Lin, L., York, D. A., Bray, G. A., Chronic effects of intracerebral ventricular enterostatin in Osborne-Mendel rats fed a high-fat diet, *Physiol. Behav.,* 54, 325-330, 1993.
36. Okada, S., York, D. A., Bray, G. A., Mei, J., Erlanson-Albertsson, C., Differential inhibition of fat intake in two strains of rat by the peptide enterostatin, *Amer. J. Physiol.,* 262, R1111-R1116, 1992.
37. Okada, S., York, D. A., Bray, G. A., Erlanson-Albertsson, C., Enterostatin (Val-Pro-Asp-Pro-Arg) the activation peptide of procolipase selectively reduces fat intake, *Physiol. Behav.,* 49, 1185-1189, 1991.
38. Ookuma, K. C., Barton, C., York, D. A., Bray, G. A., Effect of enterostatin and kappa-opioids on macronutrient selection and consumption, *Peptides,* 18, 785-791, 1997.
39. Ookuma, M. and D. A. York. Inhibition of insulin release by enterostatin. *Int. J. Obesity* 22:800-805, 1998.
40. Pierzynowski, S. G., Erlanson-Albertsson, C., Podgurniak, P., Kiela, P., Westrom, B., Possible integration of the electrical activity of the duodenum and pancreas secretion through enterostatin, *Biomed. Res.,* 15, 257-260, 1994.
41. Rippe, C, Berger K, Boiers C, Ricquier D and Erlanson-Albertsson C. Effect of high fat diet, surrounding temperature and enterostatin on uncoupling protein gene expression. *Am. J. Physiol.* 279; E293-E300, 2000.
42. Rodriguez-Gallardo J, Silvestre R A, Marco J Inhibitory effect of enterostatin on the beta cell response to digestive insulinotropic peptides. *Int J Obes Relat Metab Disord* 23(8):787-92, 1999
43. Rössner, S., Barkeling, B., Erlanson-Albertsson, C., Larsson, P., Wahlin-Boll, E., Intravenous enterostatin does not affect single meal food intake in man, *Appetite,* 34, 37-42, 1995.
44. Smeets, M., P. Geiselman, G. A. Bray and D. A. York. The effect of oral enterostatin on hunger and food intake in human volunteers. *FASEB J* 13(5):A871, 1999 (Abs).
45. Smith B. K., D. A. York, and G. A. Bray. Chronic d-fenfluramine treatment reduces fat intake independent of macronutrient preference. *Pharmacology Biochem. & Behavior.* 60:105-114, 1998.
46. Sörhede, M., Rippe, C., Mulder, H., Erlanson-Albertsson, C., Enterostatin is produced in three different forms in the rat intestine, *Int. J. Obesity,* 19, 115, 1995.
47. Tadayyon M., S Liou, C P Briscoe, G Badman, D S Eggleston, J R S Arch, D A York. Structure-function studies on enterostatin inhibition of insulin release. *Intl J Diabetes & Metabolism* 10:14-21, 2002.
48. Takenaka Y, Nakamura F, Yamamoto T, and Yoshikawa M. Enterostatin (VPDPR) and its peptide fragment DPR reduce serum cholesterol levels after oral administration in mice. *Biosci. Biotechnol. Biochem.* 2003; 67: 1620-1622.
49. Tian, Q., Nagase, H., York, D. A., Bray, G. A., Vagal-central nervous system interactions modulate the feeding response to peripheral enterostatin, *Obes. Res.,* 2, 527-534, 1994.
50. Townsley, M. I., Erlanson-Albertsson, C., Ohlsson, A., Rippe, C., Reed, R. K., Enterostatin efflux in cat intestinal lymph: Relation to lymph flow, hyaluronan and fat absorption, *Am. J. Physiol.,* 271, G714-G721, 1996.
51. Weatherford, S. C., Lattemann, D. F., Sipols, A. J., Chavez, M., Kermani, Z. R., York, D. A., Bray, G. A., Porte, Jr., D. Woods, S. C., Intraventricular administration of enterostatin decreases food intake in baboons, *Appetite,* 19, 225, 1992.
52. White C L, Bray G A, and York D A. Intragastric beta-casomorphin(1-7) attenuates the suppression of fat intake by enterostatin. *Peptides* 2000; 21: 1377-1381.
53. Winzell, M. S., M. E. Lowe, and C. Erlanson-Albertsson. Rat gastric procolipase: sequence, expression, and secretion during high-fat feeding. *Gastroenterology* 115: 1179-1185, 1998.
54. Wu, Y J, D Hughes, L Lin, D H Braymer and D A York. Comparative study of enterostatin sequence in five rat strains and enterostatin bind proteins in rat and chicken serum. *Peptides* March; 23: 537-544, 2002.
55. York, D. A, Waggener, J., Bray, G. A., Brain amine responses to peripheral enterostatin, *Int. J. Obes.,* 18, 102, 1994 (Abs.).
56. York, D. A. and Lin L. Enterostatin: A peptide regulator of fat ingestion. In: Pennington Symposium Series, Molecular Biology of Obesity, Vol. 4, pp. 281-297 (G. A. Bray and D. Ryan, eds.), Louisiana State University Press. Baton Rouge, USA, 1996.
57. York, D. A., L. Lin, B. Smith, J. Chen. Enterostatin as a regulator of fat intake. In: Neural and metabolic control of macronutrient selection. H. R. Berthoud and R. J. Seeley (eds.), Chap 20, pp 295-308, 2000. CRC Press (Boca Raton, USA).
58. York, D. A., L. Lin, B. Smith, J. Chen. Enterostatin as a regulator of fat intake. In: Neural and Metabolic Control of Macronutrient Intake, H. Berthoud, R. Seeley (eds.), Chap. 20, pp 295-308, Boca Raton, Fla.: CRC Press, 2000.
59. Berger K, Sivars U, Winzell M S, Johansson P, Hellman U, Rippe C, Erlanson-Albertsson C. Mitochondrial ATP synthase—a possible target protein in the regulation of energy balance in vitro and in vivo. Nutrit. Neurosci 5: 201-210, 2002.
60. Park M, Lin L, Thomas S, Braymer H D, Smith P M, Harrison D H T and York D A. The $F_1$-ATPase Beta subunit is the putative Enterostatin Receptor. Peptides 25 : 2127-2133, 2004.
61. Woltering E A, Lewis J M, Maxwell P J, Frey D F, Wang Y-Z, Rothermel J, Anthony C T, Balster D A, O'Leary J P, Harrison L H. Development of a Novel In Vitro Human Tissue-Based Angiogenesis Assay to Evaluate the Effect of Antiangiogenic Drugs. Annals Surgery 237: 790-800, 2003

The complete disclosures of all references cited in this specification are hereby incorporated by reference. In the event of an otherwise irreconcilable conflict, however, the present specification shall control.

What is claimed:

1. A method of inhibiting angiogenesis in a mammal with a disease associated with undesired angiogenesis, said method comprising administering to the mammal a therapeutically effective amount of enterostatin.

2. The method of claim 1, wherein the disease associated with undesired angiogenesis is selected from the group consisting of diabetic retinopathy, retinopathy of prematurity, corneal graft rejection, neovascular glaucoma, retrolental fibroplasia, epidemic keratoconjunctivits, Vitamin A deficiency, atopic keratitis, contact lens overwear, superior limbic keratitis, pterygium keratitis sicca, sjogren's syndrome, acne rosacea, phylectenulosis, syphilis, myobacterial infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, radial keratotomy, macular degeneration, sickle cell anemia, sarcoidosis, pseudoxanthoma elasticum, Paget's disease, vein occlusion, carotid obstructive disease, chronic uveitis, chronic vitritis, Lyme's disease, Eales' disease, Behcet's disease, myopia, optic pits, Stargardt's disease, pars planitis, chronic retinal detachment, hyperviscosity syndromes, toxoplasmosis, post-laser complications, abnormal proliferation of fibrovascular or fibrous tissue, hemangiomas, Osler-Weber-Rendu disease, solid tumors, blood borne tumors, acquired immune deficiency syndrome, ocular neovascular disease, age-related macular degeneration, osteoarthritis, diseases caused by chronic inflammation, Crohn's disease, ulcerative colitis, tumors of rhabdomyosarcoma, tumors of retinoblastoma, tumors of Ewing's sarcoma, tumors of neuroblastoma, tumors of osteosarcoma, leukemia, psoriasis, atherosclerosis, pemphigoid, infections causing retinitis or choroiditis, presumed ocular histoplasmosis, Best's disease, proliferative vitreoretinopathy, Bartonellosis, acoustin neuroma, neurofibroma, trachooma, pyogenic granulomas, corneal neovascularization, malignant tumor growth beyond 2 mm, benign tumors, benign functional endocrine tumors, arterial/venous malformations, primary hyperparathyroidism, secondary hyperparathyroidism, and tertiary hyperparathyroidism.

3. The method of claim 1, wherein the enterostatin is administered in a concentration from about $10^{-6}$ M to about $10^{-9}$ M.

4. The method of claim 1, wherein the disease is a non-malignant disease.

5. The method of claim 1, wherein the disease is a malignant disease.

6. The method of claim 1, wherein the prevention of angiogenesis inhibits the growth of a malignant tumor greater than 2 mm in diameter.

7. The method of claim 6, additionally comprising administering another antiangiogenic compound.

8. The method of claim 7, wherein the antiangiogenic compound is one or more different compounds selected from the group consisting of ApoA-I, HDL2, ApoA-IMilano, angiostatin, endostatin, platelet factor-4, TNP-470, thalidomide, interleukin-12, antibodies to fibroblast growth factor or vascular endothelial growth factor, tyrosine kinase inhibitors, interferons, suramin and its analogs, tecogalan, and somatostatin and its analogs.

* * * * *